United States Patent
Gehrmann et al.

(10) Patent No.: US 7,836,606 B2
(45) Date of Patent: Nov. 23, 2010

(54) STERILE FREEZING, DRYING, STORING, ASSAYING AND FILLING PROCESS

(75) Inventors: Dietrich Gehrmann, Leverkusen (DE); Ariane Firus, Pulheim (DE); Thomas Daun, Leverkusen (DE); Heinz Müller, Köln (DE); DeQian Wang, Concord, CA (US)

(73) Assignee: Bayer Technology Services GmbH, Leverkusen (DE)

( * ) Notice: Subject to any disclaimer, the term of this patent is extended or adjusted under 35 U.S.C. 154(b) by 0 days.

(21) Appl. No.: 11/572,461

(22) PCT Filed: Jul. 9, 2005

(86) PCT No.: PCT/EP2005/007455

§ 371 (c)(1),
(2), (4) Date: Oct. 3, 2007

(87) PCT Pub. No.: WO2006/008006

PCT Pub. Date: Jan. 26, 2006

(65) Prior Publication Data

US 2008/0060213 A1    Mar. 13, 2008

Related U.S. Application Data

(60) Provisional application No. 60/590,881, filed on Jul. 23, 2004.

(51) Int. Cl.
*F26B 5/06* (2006.01)
*B65D 85/42* (2006.01)

(52) U.S. Cl. ...................................................... 34/284

(58) Field of Classification Search ................... 34/284, 34/296, 298, 201
See application file for complete search history.

(56) References Cited

U.S. PATENT DOCUMENTS

| | | | |
|---|---|---|---|
| 2,441,730 A | 5/1948 | Strumia | |
| 3,162,019 A | 12/1964 | Porter et al. | |
| 3,281,954 A | 11/1966 | Baer et al. | |
| 3,313,032 A | 4/1967 | Malecki | |
| 3,397,462 A | 8/1968 | Martinis Marchi Jellicich | |
| 3,431,655 A | 3/1969 | Grover et al. | |
| 3,449,885 A | 6/1969 | Starkey | |
| 3,613,839 A | 10/1971 | MacDuff | |
| 3,648,379 A | 3/1972 | Mercer et al. | |
| 4,077,227 A | 3/1978 | Larson | |
| 4,211,015 A | 7/1980 | Adams et al. | |
| 4,323,478 A * | 4/1982 | Adams et al. | 34/305 |
| 4,608,764 A | 9/1986 | Leuenberger | |
| 4,829,783 A | 5/1989 | Buchmuller et al. | |
| 5,230,162 A | 7/1993 | Oyler, Jr. | |
| 5,737,333 A | 4/1998 | Civanlar et al. | |
| 6,584,782 B2 | 7/2003 | Leuenberger et al. | |
| 2003/0180755 A1 * | 9/2003 | Hwang et al. | 435/6 |
| 2005/0019393 A1 * | 1/2005 | Augsburger et al. | 424/464 |

FOREIGN PATENT DOCUMENTS

DE    1952381    4/1971

(Continued)

*Primary Examiner*—Jiping Lu
(74) *Attorney, Agent, or Firm*—Norris McLaughlin & Marcus PA

(57) ABSTRACT

Process for producing containers of a freeze-dried product wherein droplets of the product are frozen to form pellets, the pellets are freeze-dried, assayed and loaded into the containers.

2 Claims, 20 Drawing Sheets

SFD-SAF process

FOREIGN PATENT DOCUMENTS

| | | |
|---|---|---|
| DE | 16 25 658 | 12/1977 |
| DE | 26 25 658 C2 | 12/1977 |
| DE | 26 59 546 | 7/1978 |
| DE | 31 05 623 | 9/1982 |
| DE | 3711169 | 10/1988 |
| DE | 40 07 164 | 9/1991 |
| DE | 19654134 | 11/1997 |
| DE | 197 50 679 | 5/1999 |
| EP | 219520 | 10/1986 |
| EP | 0 219 520 B1 | 4/1987 |
| EP | 0284 837 | 10/1988 |
| EP | 429348 | 5/1991 |
| EP | 0 742 888 | 8/1995 |
| FR | 2093123 | 6/1970 |
| FR | 2 093 123 | 1/1972 |
| GB | 1 196 299 | 12/1967 |
| GB | 1482785 | 8/1977 |
| GB | 1559920 | 1/1980 |
| SU | 901782 | 4/1980 |
| SU | 901782 | 1/1982 |
| WO | WO 01/63191 | 8/2001 |

\* cited by examiner

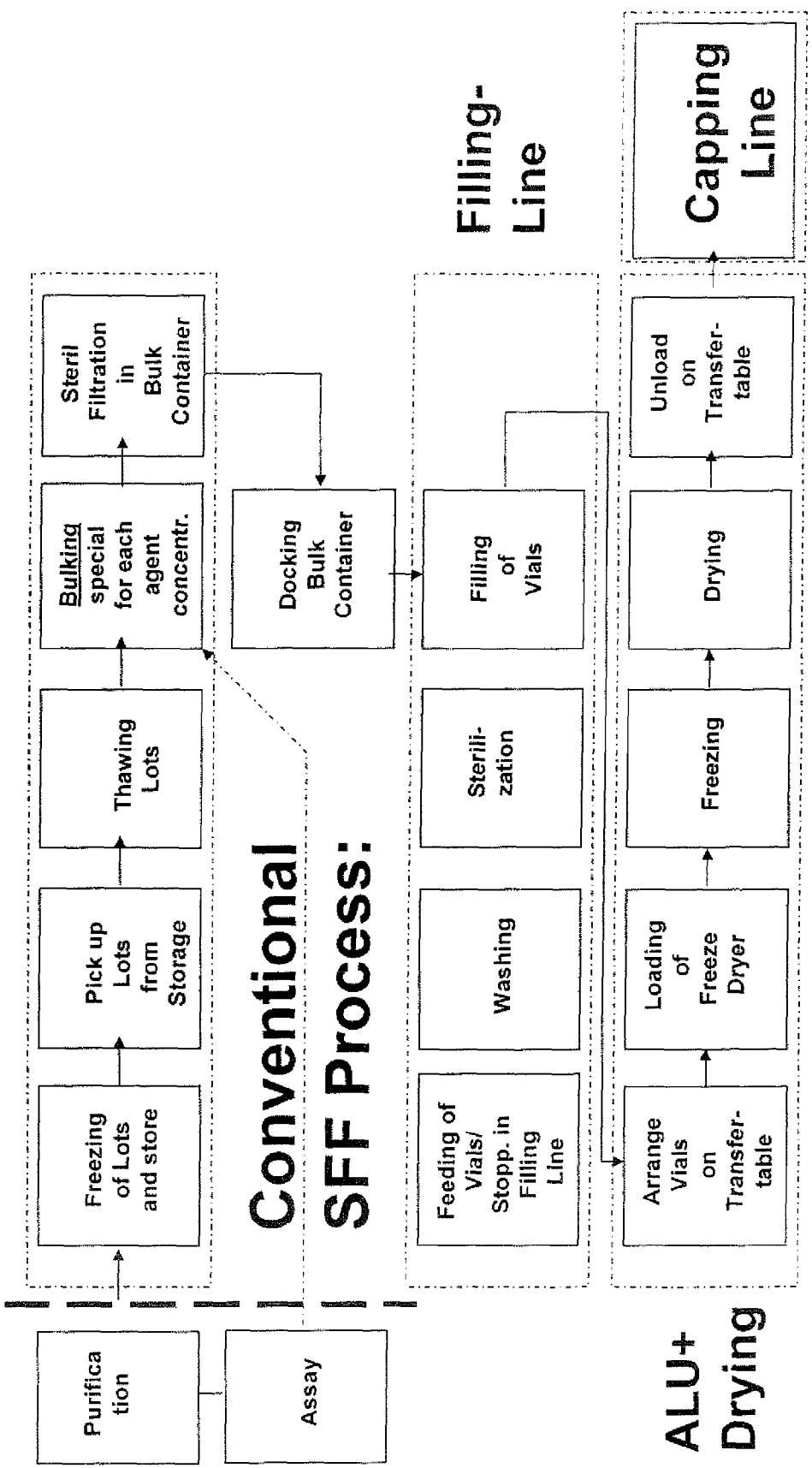
Fig. 1 The conventional Sterile Filling and Freezing Process (SFF – Process)

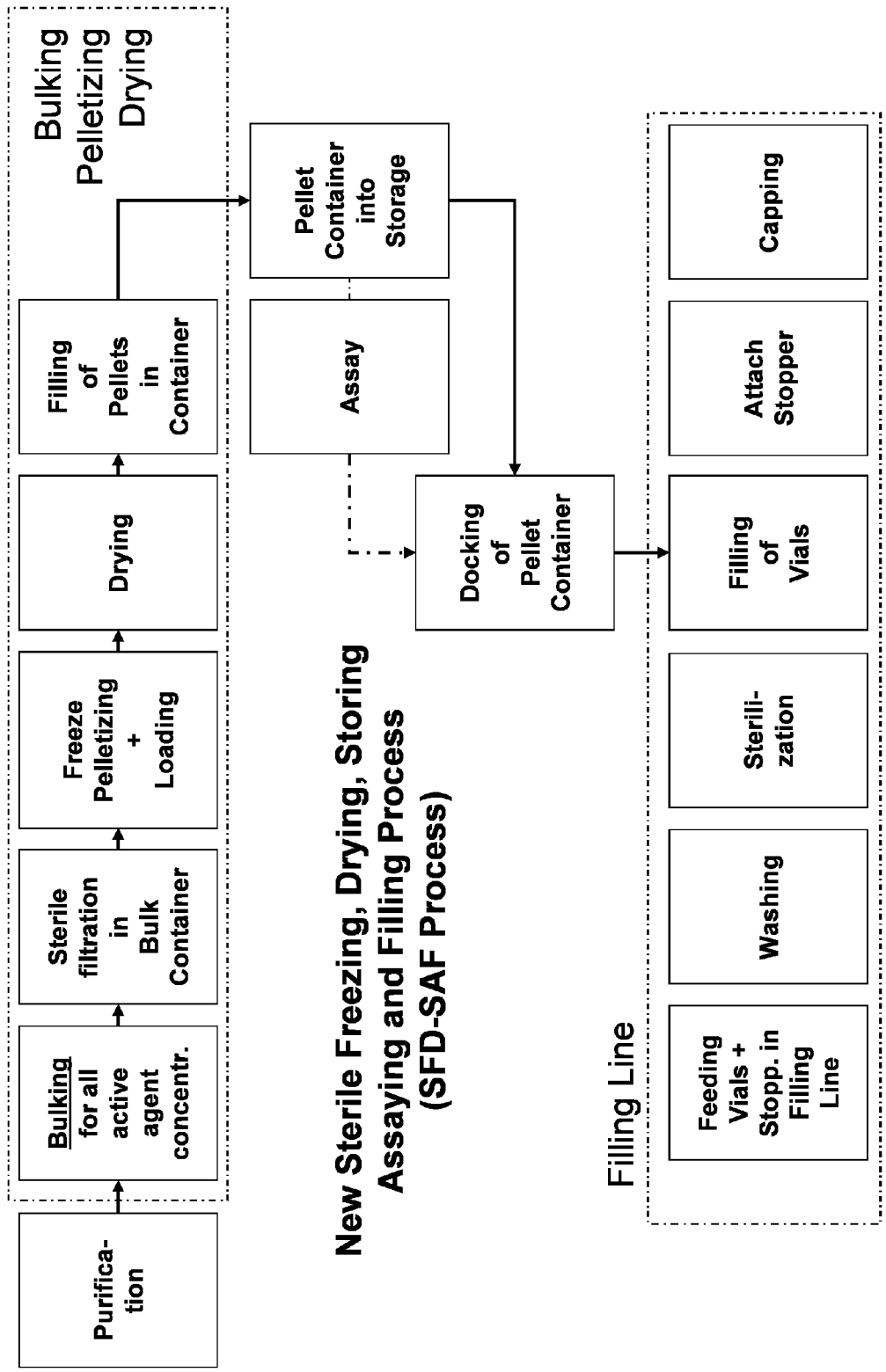
Fig. 2 The New SFD-SAF-Process

Fig. 3 steps avoided by the new process

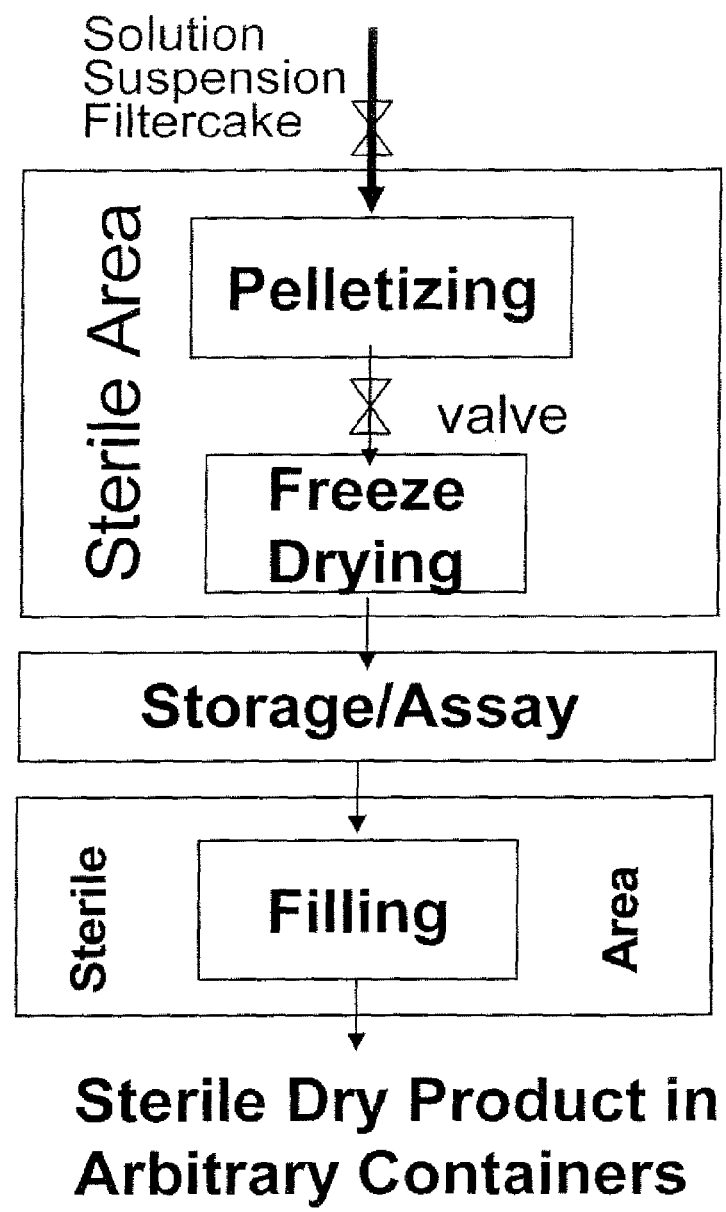
Fig. 4 Schematic SFD-SAF process

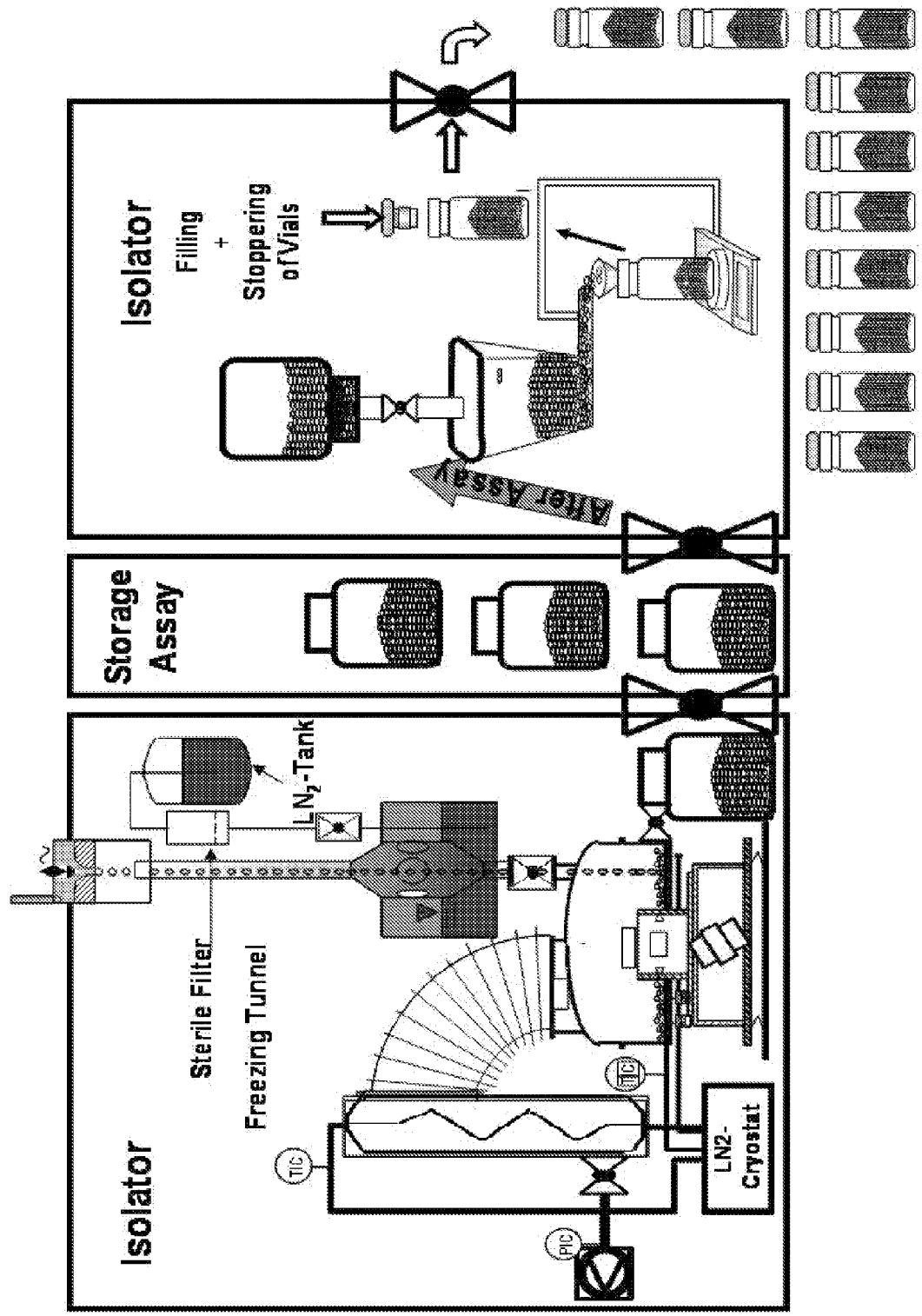
Fig. 5 SFD-SAF process

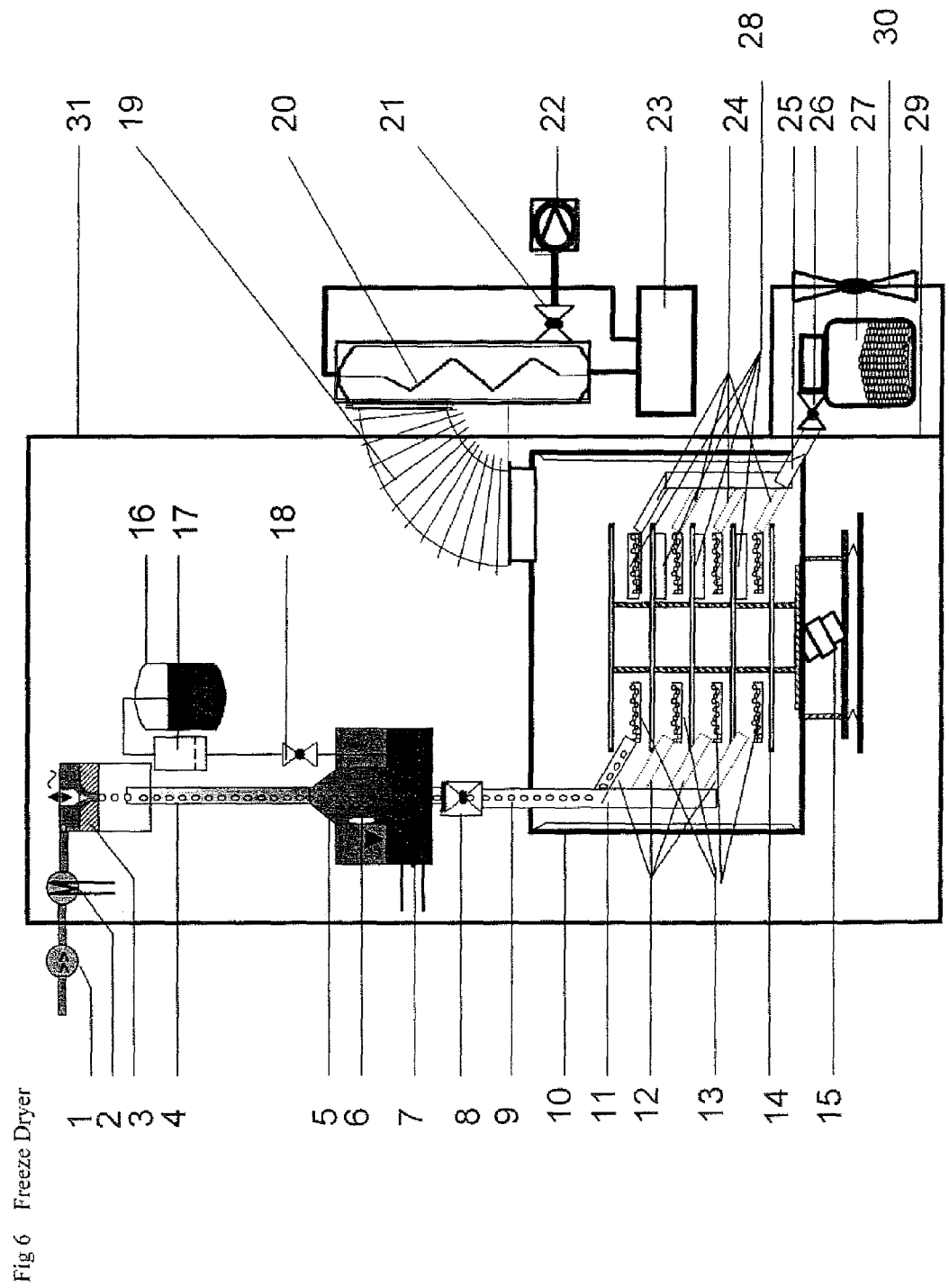
Fig 6 Freeze Dryer

Vibrating chute dosing machine

Screw conveyer dosing machine

Electro static charges hinder the continuous flow of granules in the vibrating dosing machine Fig 17 : Screw conveyer dosing:
Strong electrostatic charges hinder the dosing of granules in to vials Continuous flow of granules in the vibrating chute through ionization along the conveyer and parallel to the edge of the chute

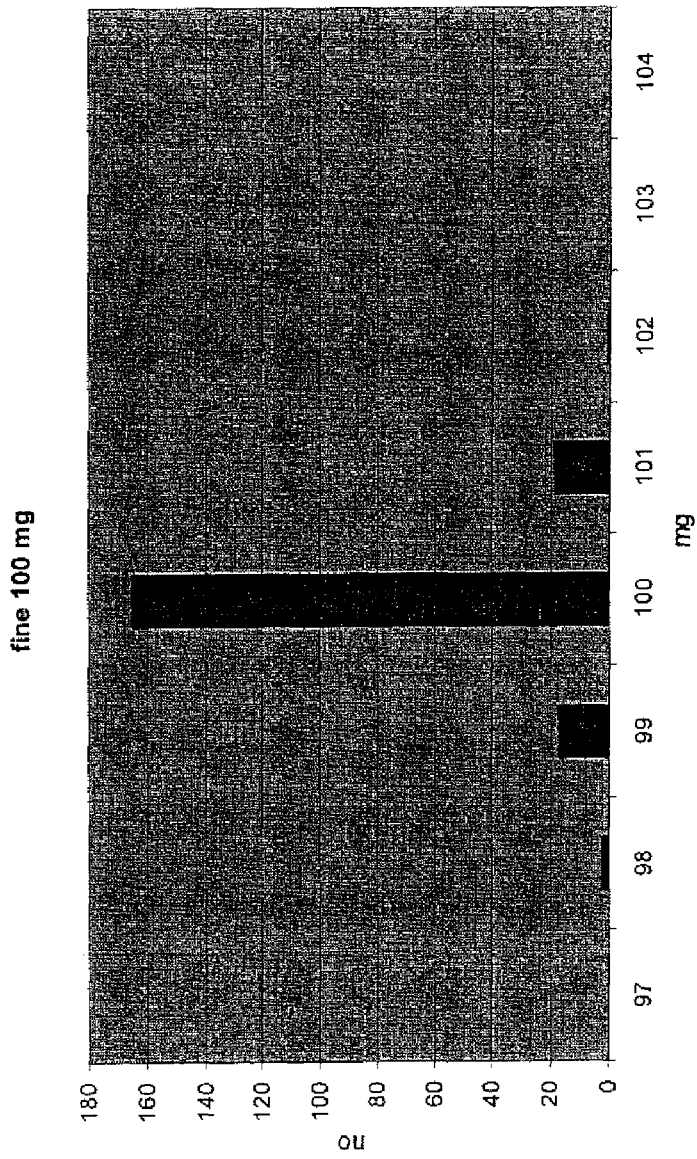
Fig. 19: frequency distribution of doses. Material: fine granules approx. 500 µm, target value 100 mg.

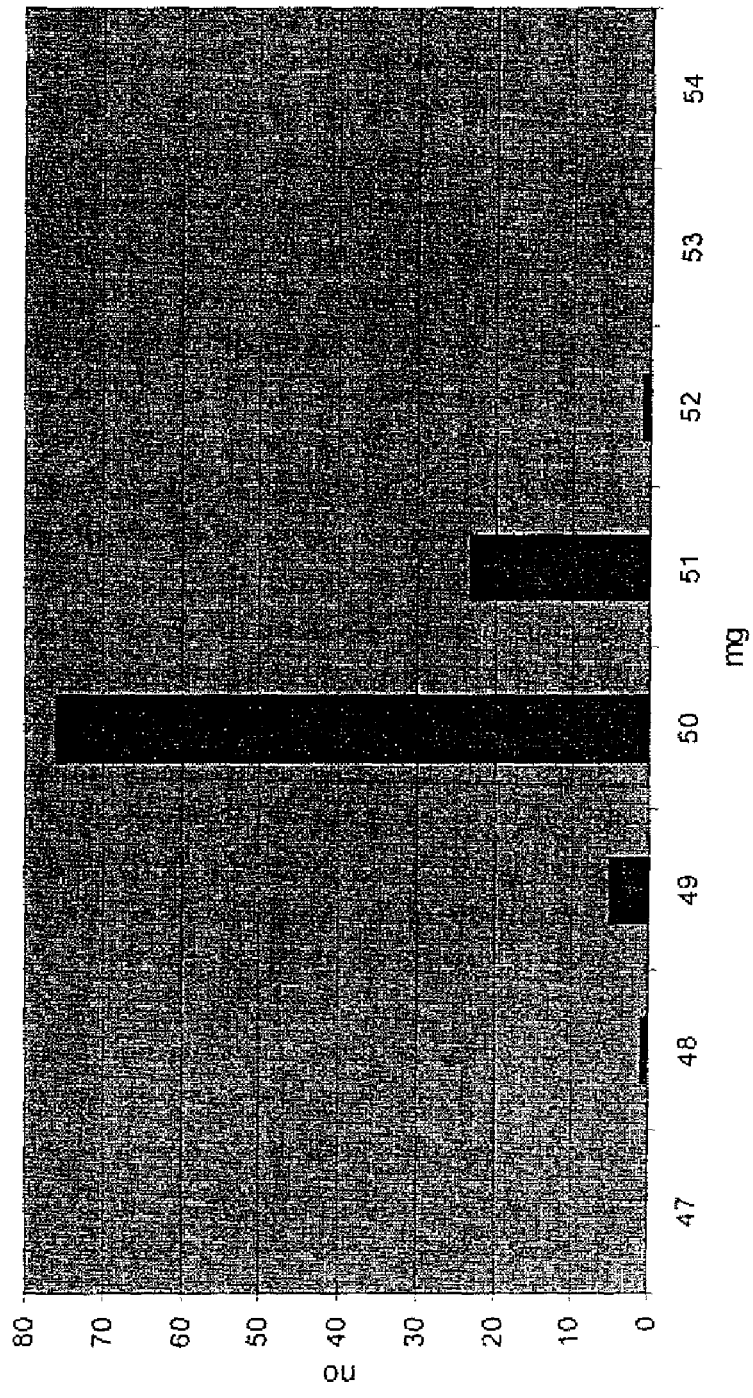
Fig. 20: frequency distribution of doses. Material: fine granules approx. 500 μm. target value 50 mg.

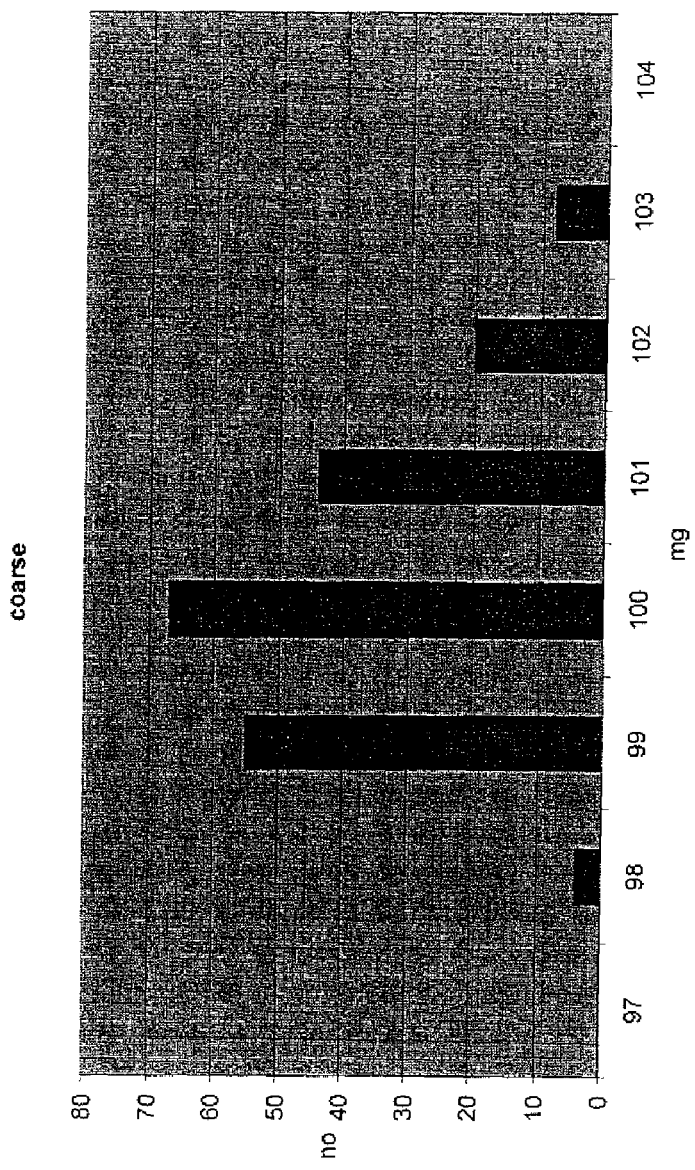
Fig. 21: frequency distribution of doses. material coarse granules approx. 1500 μm. target value 100 mg.

US 7,836,606 B2

STERILE FREEZING, DRYING, STORING, ASSAYING AND FILLING PROCESS

This is a 371 of PCT/EP2005/007455 filed 9 Jul. 2005 (international filing date).

The invention relates to a process for sterile manufacturing, including freeze-drying, storing, assaying and filling of pelletized biopharmaceutical products in final containers such as vials. The process provides on the basis of an accurate assay of the final product loaded into the final containers, and therefore more precise control of the amount loaded.

BACKGROUND OF THE INVENTION

The conventional process for manufacturing and packaging parenteral biopharmaceuticals involves the formulation of a bulk solution in accordance with the measured biological activity of the intermediate material used to formulate the bulk solution. In many cases, particularly at the end of the process, the bulk solution is frozen and stored for making the assay. For this purpose the frozen solution may be stored for several days or even for several weeks. For the subsequent filling of the final packages, such as vials, for e.g. distribution to the end users, the frozen intermediate solution is typically thawed, bulked and loaded into e.g. vials, and then freeze-dried within the vials.

The amount of thawed bulk solution that is loaded into the final packaging e.g. vials, is calculated on the basis of the assay of the intermediate solution. This calculation usually incorporates a large safety margin because of (1) large variation of biological assay and (2) loss of yield in the subsequent sterile fill and freeze-drying process. The loss of yield is due to product stress during this first freezing, storing and thawing step and the following second filling, freezing and drying process. This calculation is of course very difficult and based on product dependent empirical knowledge of the complete process.

In accordance with the heretofore known processes (as shown in FIG. 1), the active agent solution is assayed after the final purification step and then frozen in identified individual lots—consisting of several bags—and stored or shipped for subsequent use. The frozen formulation is then thawed, bulked and then filtered and transferred to bulk containers. The bulk containers are then positioned in a production line, and the liquid product in the bulk containers is then loaded into e.g. individual vials, in the calculated amounts. Prior to filling, the vials are usually washed and sterilized. The loaded (i.e., filled) vials are then arranged on a transfer table, loaded into a freeze-dryer, frozen in an appropriate freezing process, dried in an appropriate drying process, unloaded from the drying process into a transfer table and transferred to a capping line where they are sealed.

The conventional process is an addition of singular processes and technologies which are described in several patents and publications. Novel literature like "Freeze Drying" by G. W. Oetjen, Wiley-VCH, 1999, pages 127-195 describes very accurate and detailed the current state of the art. There are additionally several patents which describe these singular technologies.

U.S. Pat. No. 2,441,730 describes a shell freezer and a dryer which dries the product from the frozen state. In a shell freezer the product is frozen on the inside walls of an axial rotating vial. U.S. Pat. No. 3,281,954 describes a freeze dryer for bulk material which is filled into trays as a solution. These trays are arranged on temperature controlled shelfs and frozen at low temperatures. Than the frozen product is freeze dried and unloaded into a container.

U.S. Pat. No. 3,397,462 describes an apparatus for lyophilization of substances containing an aqueous phase. This patent describes a hermetic sealable cell loader which contains the containers, vials or ampoules filled with sterile solution. This cell loader can be used for prefreezing and subsequent sterile transport of the frozen product into the freeze dryer.

EP 429348 describes a small bottle loading apparatus such as for freezedrying plant. Bottles are collected and stocked on a vibrating table, with a device moving them on to the vibrating table tray. This is a claimed method for transferring filled containers with a loading device into the freeze dryer.

EP 219520 describes an industrial, mechanical handling truck for transferring flat plates or trays on to the horizontal shelves of a processing chamber, e.g. a freeze-drying chamber.

A block diagram of a typical prior art process is shown in FIG. 1. As is shown, the freeze-drying process is usually performed in standard freeze drying chambers which do not have temperature controlled walls. These dryers, unfortunately, provide non homogeneous heat transfer to the vials placed in the dryer chamber. Especially, those vials which are positioned at the edges exchange energy more intensively than those positioned in the center of the plates, due to radiant heat exchange and natural convection in the gap between the wall of the chamber and the stack of plates/shelves. This non-uniformity of energy distribution leads to a variation of freezing and drying kinetics between the vials at the edges and those in the center, and could result in variation in the activities of the active contents of the respective vials. To ensure the uniformity of the final product, it is necessary to conduct extensive development and validation work both at laboratory and production scales.

Therefore there has been a long felt need for a process which avoids the above mentioned disadvantages. The present process fulfills that need.

SUMMARY OF THE INVENTION

In accordance with the present invention, there is now provided a process wherein fine droplets of the bulk solution are frozen to form frozen pellets, the frozen pellets are freeze-dried, homogenized if desired, assayed and loaded into final containers; all under sterile conditions. Optionally, the freeze-dried pellets may be stored prior to or after homogenizing and/or assaying.

The present process is therefore based on four steps (FIG. 4): 1. Creation of frozen pellets 2. Freeze drying of those pellets 3. Storing, homogenizing and assaying the freeze dried pellets 4. Filling those pellets in final containers based on the assay result of the pellets and thereby eliminating any overfill. All Steps are carried out under sterile conditions.

BRIEF DISCUSSION OF THE DRAWINGS

FIG. 1 illustrates the conventional prior art Sterile Filling and Freezing process (SFF process).

FIG. 2 is a block diagram of a preferred embodiment of the present invention.

FIG. 3 illustrates those steps of the conventional prior art process which are avoided by the present process.

FIG. 4 is a schematic of the Sterile Freezing and Drying-Storing, Assaying and Filling Process (SFD-SAF).

FIG. 5 is a flow chart of an embodiment of the present invention wherein the frozen pellets are created in a freezing tunnel.

FIG. 6 illustrates details of the dryer shown in FIG. 5, including the temperature controlled plates.

Figure 8:
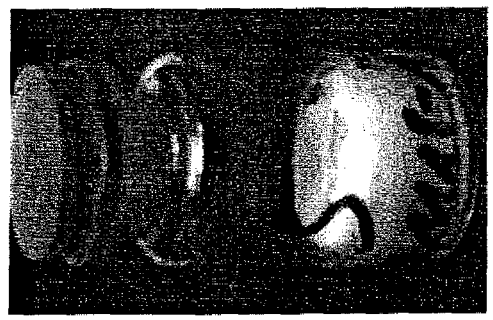
FIG. 8 is a photograph of a product produced by the conventional prior art process, wherein a product is freeze-dried in vials.

FIG. 19 is a graphical representation of the distribution of doses among 200 vials loaded with a target dose of 100 mg. of fine granules by the process of the present invention FIG. 20 is a graphical representation of the distribution of doses among 100 vials loaded with a target dose of 50 mg. of fine granules by the process of the present invention FIG. 21 is a graphical representation of the distribution of doses among 100 vials loaded with a target dose of 100 mg. of a mixture of coarse and fine granules by the process of the present invention

DETAILED DESCRIPTION

There are many methods known to those skilled in the art by which frozen pellets may be produced.

U.S. Pat. No. 3,162,019 describes a process where pellets are produced by dropping a liquid formulation into a low temperature liquid having a boiling point lower than the freezing point of the solution.

The frozen pellets are then separated from the cooling liquid by a separation means and transported into a sublimation dryer.

U.S. Pat. No. 4,077,227 describes means for the production of droplets which are subjected to an electric field of sufficient strength so as to induce on each drop an electric charge of the same polarity. These charged droplets are directed onto the surface of a cryogenic liquid where they momentarily float while being transformed to a solid frozen state. During this time the electric charges of like polarity inhibit agglomeration, so that each droplet sinks as an individual pellet.

EP 0284 837 (U.S. Pat. No. 4,829,83) describes a process for the production of frozen pellets with a narrow particle size distribution. The droplets are created by two perforated metal plates which can be positioned so that the open area of the two holes varies with the varying position of the metal plates. The outlets of the holes are specially designed in order to create a nearly uniform droplet size distribution. These droplets fall into a cryogenic fluid where they become transformed into a solid frozen state.

DE 40 07 164 describes a process for the production of frozen flowable particles by using a two fluid nozzle which creates droplets of a certain size distribution. These droplets are directed onto a surface of a cryogenic liquid. By varying the pressure of the propellant gas and/or the liquid solution/melt the droplet size distribution can be varied over a wide range so that the production of very fine frozen powder is possible.

DE 31 05 623 describes a process which uses a centrifugal atomizer for the production of droplets which are directed into a stream of liquid nitrogen produced by nozzles arranged on the top of the chamber. The droplets falling concurrent with the liquid nitrogen are transformed during the falling time into a frozen state and are gathered as frozen pellets at the bottom of the chamber for further transportation into a vacuum chamber.

DE 26 59 546/GB 1,559,920 describes a process for the creation of frozen droplets by concurrent spraying of droplets into a stream of boiling liquid coolant. The droplet size can be controlled by varying the viscosity of the spray solution and/or the injection pressure and diameter of the nozzle. The frozen droplets are gathered at the bottom of the spray tower by a conveyer, which transports the frozen particles into a continuous working freeze dryer.

DE 197 50 679 describes several processes for the creation of frozen droplets in spray towers working with injection of liquid gases, such as liquid Nitrogen. The droplet spray changes into a solid frozen state during falling with con- or counter current cooling gas streams and are gathered at the bottom of the spray tower.

U.S. Pat. No. 5,230,162 (Oyler, 1993) describes a process in which spray droplets are created in a first spray chamber with cooled air at atmospheric pressure. The droplets change into frozen state during their falling time and are metered through a vacuum lock into a second evacuated chamber which serves as a freeze dryer.

EP 0 742 888 (U.S. Pat. No. 5,737,333) describes a process in which a spray is created in an evacuated spray tower. The solution is precooled to a suitable temperature taking into account the super cooling behavior of the solution. Further cooling of the droplets is forced by sublimation cooling in the vacuum chamber. The final droplet temperature is determined by the vacuum pressure in the spray chamber and the sublimation/boiling temperature of the solvent content of the droplet at this vacuum pressure. The vacuum pressure has to be selected so that the final droplet temperature is certain degrees lower than the freezing point of the solvent. The frozen droplets are collected at the bottom of the chamber on a collecting surface and freeze dried in the existing vacuum. The temperature of the collecting surface is controlled at a temperature which will prevent any remelting.

GB 1 196 299 (Nestle, 1966, 1970) describes a continuous working freeze dryer for particulate material, which comprises a vacuum chamber, a support for frozen particulate material within the chamber, means for vibrating the support, at least one heating device for heating the frozen material to sublime volatile solids contained therein, at least one vapor outlet for removing sublimed vapors from the chamber and at least one filter for retaining fine particles removed from the frozen material. This filter is arranged within the chamber between the support and vapor outlet. The heater is integrated into the support which serves as a tray for the frozen Particulate material.

DE OS 26 25 658 describes a freeze dryer for particulate material comprising a chamber with several plates arranged one upon another. The product is moved from the top to the bottom plate. The area of each plate is enlarged a certain amount from top to bottom. The surface for the particulate material can also be designed as a spiral with continuously varying diameter from top to bottom. The top diameter is the smallest while the bottom diameter of the spiral is the largest. These varying diameter are due to the vapor production on each level of the dryer. In order to avoid pressure gradients across the surface of the particulate material the pressure drop due to the vapor flow is minimized by adaptation of the diameter and the gap between all plates.

FR2093123 describes a freeze drying chamber with an arrangement of platforms with varying depth of the frozen particulate material in order to minimize sputtering of the granules by rapid evolution of vapor from the lower part of a relatively thick bed of granules onto the walls of the vacuum chamber.

DE 3105623 describes a process for creating frozen particulate material and a freeze dryer connected with the chamber for the production of frozen particles by a vacuum-tight metering device. The continuously working freeze dryer consists of heated conveyers transporting the frozen subliming particulate material and a low temperature condenser for condensing the vapors.

SU 901782 describes a tray type sublimational freeze dryer with heat conducting elements made as finned rods containing electrical elements to intensify the heat transfer. The tray vibrates to keep granules of product moving.

U.S. Pat. No. 5,230,162 (Oyler, 1993), also discussed above with respect to freeze-pelletizing, describes a spray freeze drying process in which the spray is frozen in a first chamber by using cold gas for the freezing process of the fine spray droplets. The frozen particulate material is metered by a vacuum lock in to a second evacuated chamber with heated walls. The fine distributed frozen powder sublimes due to the radiation heat exchange between heated walls and frozen powder and has to be completely dried while it falls down to the bottom of the column. The dry powder leaves the tower by a second vacuum lock into an evacuated container.

DE 1952381 describes a freeze dryer comprising a vacuum chamber with inverted, vertically spaced and laterally staggered downwardly inclined and oppositely disposed cascade elements which are heated to warm the frozen granulate and evaporate the moisture from it. The elements are spaced such that they form vapor extraction channels and granulate supporting members, in which granulate is deposited in layers, which are moving across the members continuously or intermittently.

U.S. Pat. No. 3,648,379 describes a freeze dryer especially designed for freeze drying coffee which consists of a conveyer cooled to −40° C. so that the solution distributed on the surface of the conveyer is frozen. The frozen solution is coarsely broken and then ground to required grain size distribution. The particles are introduced via a vapor lock into a freeze drying chamber containing a number of horizontal conveyors that are longitudinally vibrated at their resonance frequency to vibrate the particles and expose their surfaces.

U.S. Pat. No. 4,608,764 describes a freeze drying process in a fluidized bed. The particulate material is fluidized by a cooled gas in order to maintain the frozen state of the particles. Using dry gas with a dew point temperature lower than the gas temperature the frozen material can sublime the frozen humidity.

WO 01/63191 (U.S. Pat. No. 6,584,782) describes a freeze drying process working in a pair of fluidized bed dryers connected to each other. Each fluidized bed chamber is provided with filter bags for retaining fine particles entrained with the freezing fluid. The first fluidized bed chamber produces frozen particles/granules by spraying droplets into a fluid of appropriate temperature to freeze them into frozen particles. These particles are then dried by lyophilization in the next fluidized bed chamber. For the purpose of lyophilization, a cooled (conditioned) process gas is led through the process chamber and the filter from the bottom to the top in such a manner that at least a substantial part of the particles is contacted with the filter at least during a substantial interval of the lyophilization proceeding in the process chamber. Due to the high heat transfer between particles and cooled gas the process allows drying a batch of particles very quickly.

DE 19654134 (U.S. Pat. No. 3,613,839) describes a freeze dryer for biological material in a slowly rotating drum. The inner wall of the drying chamber is heated and slowly rotated. Vapors released by sublimation are withdrawn. The process is suitable for frozen granules or pellets.

Advantageously, the present process (1) eliminates the need for final product overfill, previously necessitated by the uncertainties arising out of a large variation in the biological assays (usually >±110%) for biopharmaceutical products.

(2) enhances product yield and improves homogeneity of the freezing-drying process, (3) makes it possible to fill the final containers with user-defined active content, (4) reduces the formulation process to the preparation of only one single formulation for arbitrary amounts of actives per final container (vial), (5) opens the possibility of filling different amounts of several different dry actives in each final container (vial) in order to create a multipurpose drug, (6) provides homogeneous dry product on the basis of the following essentials:

The freeze-drying process can be performed as a batch as well as a continuous process, The process uses pellets instead of freeze dried cakes in vials Pellets with a narrow particle size distribution are frozen under uniform process conditions so that each pellet is subjected to the same freezing and drying temperature conditions resulting in homogeneous microstructures inside each pellet as well as within the total of all pellets, The homogeneous pellets are dried in a freeze dryer providing homogeneous drying conditions, which avoids edge effects and inhomogeneous partial pressures inside the drying chamber, Due to the homogeneous freezing and drying conditions in the product matrix (pellets have very small dimensions in comparison to vial cakes) damage to the product is minimized, (7) The freeze dried pellets are filled in containers and, if necessary or desirable, may be homogenized by a gentle mixing process to provide a homogeneous consistency of the content and uniformity of quantity which is filled into the containers.

(8) since the bioactivity of the final pellets is known, product overfill caused by the uncertainty of biological assay in the prior art can be avoided.

(9) Due to the homogeneity of the freeze dried pellets and the known assay, the previously required margin of error is no longer necessary to ensure a sufficient content of active ingredient per final container (vial),

(10) Due to the stability of freeze dried pellets it is possible to provide a combination of different dried drugs in each vial in order to obtain a multipurpose drug/medicine/vaccine.
(11) The production of freeze dried pellets may be completely independent of the Filling and Capping process,
(12) The filling process is based on powder fill technology, which has an accuracy comparable to that of liquid filling systems Creation of frozen pellets can be performed with any of the known technologies, such as those described above technologies preferably e.g. with continuously or batch-wise working apparatus, such as "Kryogen Rapid Pelletizer" from Messer-Griesheim, Germany or "CRYOGENIC PELLETIZER" from IQFCRYOGRAN, Canada. Due to the subsequent freeze drying step, the frozen pellets should have a narrow particle size distribution in the range of 500 µm<$d_{50}$< 1500 µm preferably 1000 µm. After isolation, the frozen pellets can be transported under sterile and cold conditions to a freeze dryer. The pellets are then distributed across the carrying surfaces inside the drying chamber. The distribution across the carrying surface is accomplished, for example, by a distribution device, such as a vibrator, in order to provide a homogeneous pellet layer.

In order to achieve homogeneous drying conditions, the heat exchange between heat sources and pellets should be uniform. Edge effects can be avoided by temperature controlled walls. Sublimation drying is in principle possible in any kind of freeze dryers suited for pellets, such as those described above. Freeze dryers providing space for sublimation vapor flow, controlled wall temperatures and suitable cross sectional areas between drying chamber and condenser are preferred. None of the heretofore known conventional dryers provide the foregoing combination of properties completely. Therefore the present invention also concerns a design fulfilling all the foregoing demands. FIG. 6 illustrates the elements of an integrated Kryopelletizer and Freeze Dryer according to the invention.

In FIG. 6:
1) is a pump for the bulk solution
2) is a heat exchanger for temperature control of the solution to be cryopelletized.
3) is a frequency assisted droplet producer for the production of uniform droplets. It can work with one nozzle or a multiple of nozzles depending on the production rate. The droplet size is dependent upon the nozzle diameter in first order.
4) is an isolated tunnel long enough to provide a suitable residence time for the cooling and freezing of the falling droplets.
5) is a cylinder which separates the cryogen liquid from the gas filled zone
6) are openings for the cryogen gas generated from the boiling cryogen liquid. This gas flows partly counter current to the falling droplets and partly into the drying chamber according to the flow resistance
7) is a boiling chamber with cryogen liquid and heat exchanger for the continuous generation of a cryogen gas flow
8) is a valve for controlling the gas flow into the drying chamber
9) is a feeding tunnel for the frozen pellets
10) is a drying chamber with controlled wall temperatures
11) is a guide for directing the frozen pellets onto a pellet carrier surface
12) are feeder channels for single or multiple pellet carriers
13) are single or multiple pellet carriers
14) is a heating plate for radiation heat transfer to the pellet carriers
15) is a vibrator for vibrating the drying chamber
16) is a storage container for cryogen liquid
17) is a sterile filter for Cryogen liquid
18) is a valve for separating the cryogen fluid tank from the freezing tunnel
19) is a flexible connection between drying chamber and condenser
20) is a cold trap
21) is a valve for connection/disconnection of the vacuum pump from the freeze dryer and condenser
22) is a vacuum pump
23) is a cryostat
24) are channels for unloading the pellet carriers
25) is a channel for feeding the storage containers
26) is a sterile connection between feeder channel and storage container
27) is a storage container
28) are guides for directing the freeze dried pellets into the channels for unloading the pellets
29) is an isolator housing
30) is a sterile docking station for unloading the storage container (27)
31) is an isolator containing the freezing and drying facilities As illustrated, the final bulk solution is dosed from a bulk container (not shown here) by pump (1) or by pressure into the frequency assisted droplet producer (3). This solution is cooled by heat exchanger (2) to a product dependent temperature above the super cooling temperature. The droplet producer (3) can be a single nozzle or a multiple nozzle unit as described above. The number of nozzles is dependent on the designed production rate. The droplets fall into the freezing tunnel (4) counter current to the cryogen gas streaming up from the cylinder (5). The cryogen gas is generated in the boiling chamber (7) with integrated heat sources for a steady production of cold cryogenic gas. This cold gas, such as liquid nitrogen generated at ≈−180° C., is used for cooling down and freezing the falling droplets as well as for cooling down the drying chamber (10) and the pellet carrying surfaces. Valve (8) controls the gas flow into the drying chamber (10) before the cryo pelletizing process begins. If all pellet carrying surfaces (13) have the necessary temperature below the freezing point of the pellets the cryo pelletizing process can start. Valve (21) is closed in order to stop the flow of cold gas through the drying chamber (10). Valve (8) is completely opened in order to let the falling frozen droplets pass into the feeding tunnel (9). Now the guide (11) positioned at the entrance of each pellet carrying surface (13) is opened and the falling frozen pellets trickle through the feeding channels (12) onto the pellet carriers. For spreading the pellets across the carriers the whole drying chamber is vibrated by the vibrator in short intervals (15). As an alternative, only the pellet carriers (13) are vibrated by an integrated separate vibration system (not shown here). These intervals are product dependent and are limited by the mechanical stability of the pellets. After the filling of all pellet carrying surfaces (13) the thermal treatment can start. By heating the heat sources (14) and corresponding cooling by cryogen gas via valve (8) and corresponding wall cooling the pellet layers can be treated with any suited temperature-/time program. After thermal treatment the freeze drying process can be started. Valve (8) is closed. The condenser (20) is cooled down to the designed temperature. Valve (21) is opened and the vacuum pump (22) starts the evaporation process. The heating sources (14) start their temperature/time program and the wall temperatures are adjusted to a temperature corresponding to the pellet temperatures. In dependence on the mechanical stability of the pellets the pellet carriers can vibrated in certain intervals. If the pellets are mechanically very unstable, the vibration intervals have to be minimized. In order to decouple the vibrated pellet carriers (13)/drying chamber (10) from the condenser (20) a flexible tube (19) connects drying chamber (10) and condenser (20). After finishing the sublimation cycle the pellets are unloaded. A sterile storage container is docked to the sterile valve (26). Vibration allows the pellets to move around the centre of the freeze dryer. Weirs (28) are moved down into each layer—one after another—or all at the same time (product dependent) guiding the moving pellets into the unloading channels (24) and then into the channel for feeding the storage container (27). The storage container (27) is then transferred into an isolator. A statistically relevant number of samples are taken from each storage container (27) for performing an assay. After that the storage container (27) is packed into a sterile containment and transferred into storage. After assaying the content of each storage container (27) all necessary properties such as e.g. actives content are known. The filling process into the final containers with the user defined amounts of pellets can then begin. The storage containers (27) are transferred to the isolated filling line and docked at the sterile docking station. The contents of the containers are transferred inside the isolator to the storage of the filling machine. In case of bulked solutions with very low super cooling temperatures and/or problematic freezing kinetics an alternative for the pellet freezing is provided (not shown in FIG. 6). In this case the droplets are made to fall into a container having a cryogen liquid, where they remain for a sufficient time to achieve a complete frozen state. Due to the deep temperature of the droplets at the end of the freezing tunnel (4) and a normally frozen droplet surface the possibility for agglomeration in the cryogen liquid is minimized. The pellet size distribution remains nearly unchanged. The principles of this technology are described above. Useful apparatus is available from appropriate manufacturers. After isolation, the frozen pellets are dosed by appropriate conveyers (e.g. vibrating chute) into the feeding tunnel (9).

The differences between the conventional process and the present process is demonstrated by FIG. 2. From a comparison of the new SFD-SAF process to the conventional processes, it can be seen that the steps shown in FIG. 3 are avoided:

Particular advantages of the new process are: (1) it does not require any kind of Automatic Loading and Unloading (ALU) system, (2) it requires only one bulking step, and (3) it is more flexible to allow filling and capping to be done at different time and locations.

The invention is particularly useful in the preparation of parenteral biopharmaceuticals as a pellet-based product.

FIG. 4 illustrates a schematic of such a process. The creation of frozen pellets, drying and filling the particulate material obtained in storage containers has to be performed under sterile conditions.

FIG. 5 shows an embodiment of the process of the present invention in which frozen pellets are created in a freezing tunnel.

In the process shown in FIG. 5, the temperature of the solution is cooled down to a temperature point above the super cooling temperature. The droplets are produced with known frequency assisted nozzles. The preferred size of the frozen particles is between 500 and 1500 µm. The liquid droplets change into the frozen state as they fall through the counter-current flow of cryogenic gas. The cryogenic gas, preferably liquid nitrogen from an outside mounted tank, is sterile filtered and placed in a vessel with heating elements for a steady boiling process in order to provide a sufficient and steady mass flow of cold gas counter current to the falling droplets. At the end of the freezing tunnel the frozen particles fall onto a cooled surface in the dryer which can be vibrated continuously or intermittently over short time intervals. The vibration is used for spreading the frozen particles across the whole cooled surface in order to get a homogeneous particle layer. The vibration can also be used for continuous particle movement around the centre of the cooled surface. The cooling temperature for the frozen layers is adjusted by temperature controlled plates or by cooled gas so that any partial melting of the frozen particles is avoided.

The dryer has either one temperature controlled surface for the layer or a plurality of temperature controlled plates as shown in FIG. 6. The dryer can also be designed as a conveyer dryer with one conveyer or with a plurality of conveyers (not shown). Such dryers are available from e.g. by GEA NIRO ATLAS The dryer used may also be a chamber dryer, such as is conventionally used for vials. In this case the product carriers are trays which are filled outside the dryer and then placed between the temperature controlled shelves so that no direct contact between tray and temperature controlled shelf occurs. The heat required for sublimation is preferably produced by radiation only.

After filling the product carriers with frozen pellets, any type of thermal treatment, such as an annealing process for crystallizing bulking agents can be performed. After this treatment the sterile connections between the feed containers and the freezing and drying equipment can be closed and the closed drying chamber can then be evacuated, and the sublimation started.

For improved heat transfer and mixing of the product layer, the continuous vibration of the product carrying surface is preferred. This depends on the mechanical stability of the pellets, however. The vibration process can generate fines due to frictional effects. If the particular product is susceptible to the formation of undesirable amounts of fines by this mechanism, the vibration should be used in short time intervals only, to minimize the generation of fines. In this case vibration serves primarily for distributing and homogenizing the layer during the filling and the unloading process.

For homogeneous drying of the particulate product layer(s) all energy transferring areas should be temperature controlled with a limited temperature difference across these areas. These differences should be in the range of ±1.5° C. To provide minimal pressure differences in the drying chamber, the vapor flow velocity should be limited to a relatively low level, depending e.g. upon the fluidization of the particles. That means that all vapor flow ducts have to provide suitable cross sectional areas. The same applies to the cross section of the vapor ducts between the drying chamber and the condenser. In case of a long dryer, such as e.g. a conveyer dryer, a plurality of vapor ducts between the drying chamber and the condensers may be required.

In order to minimize edge effects, the wall temperatures are controlled so that there is no additional driving potential for heat transfer between the walls and the exposed product near the walls.

A second possibility for the production of frozen pellets with a desired range of particle size diameter is the external/separate production of the pellets either in a freezing tunnel (FIGS. 5, 6) or in another known process such as is described in several patents e.g. DE 3711169 (=U.S. Pat. No. 4,829, 783). The frozen pellets are then transported in a cooling chain to a cooled loading tunnel with a sterile connection to a cooled frozen pellet container. The frozen pellets can than be metered by a metering device to one or more product carrier surfaces (trays).

In the embodiment illustrated in FIG. 6, the dry product is moved by a gentle vibration across the surface of one or more trays and led by a weir into an unloading tunnel. A container for the dry product is connected via a sterile connection to the unloading tunnel of the dryer.

The container with dry pellets may, if desired, be homogenized by a gentle mixing and rotating, and then stored and assayed.

By this method, very accurate information such as mass, density, actives content and other important final product properties may be obtained for the contents of the containers. This information can be used for the release of final product having very exact activity.

The last step of filling the dry pelletized products into final containers can be done using known filling machines, such as those available from Fa. Bausch+Stroebel, Bosch, Harro Höfliger or others.

This present process is especially useful for formulations of sensitive bioactive compounds, such as vaccines, enzymes and various proteins.

Due to the very homogeneous bulk pellet product achieved by the process, it is possible to reduce the overfill of containers (i.e., to account for a margin of error), with respect to the target content, to less than 10%, preferably less than 5%, particularly preferably less than 2% and most preferably to 0%. This is, of course, affected by the accuracy of the filling process/machinery used for the final containers. The overfill necessary to compensate for any deviation of said filling process machinery must still be taken into consideration.

Containers, preferably vials, sterile filled with sterile freeze dried pellets with less than a 10%, preferably less than a 5%, particularly preferably less than a 2% margin of error (i.e., overfill), with respect to the target content is also the subject to the present invention.

EXAMPLES

Example 1

Production of Frozen Pellets

Figure 7:
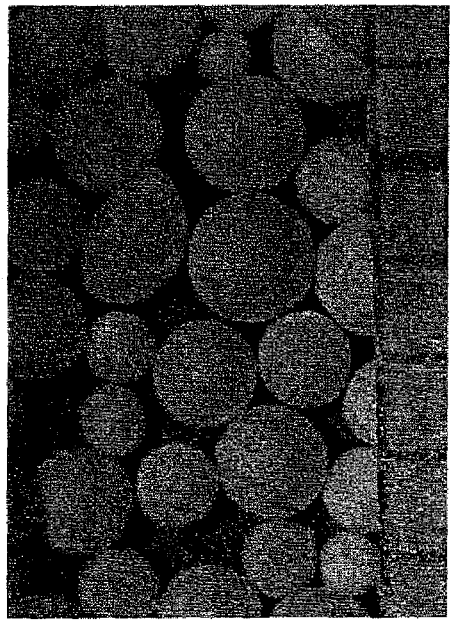
FIG. 7 is a photograph of a product produced by the present process.
Figure 9:
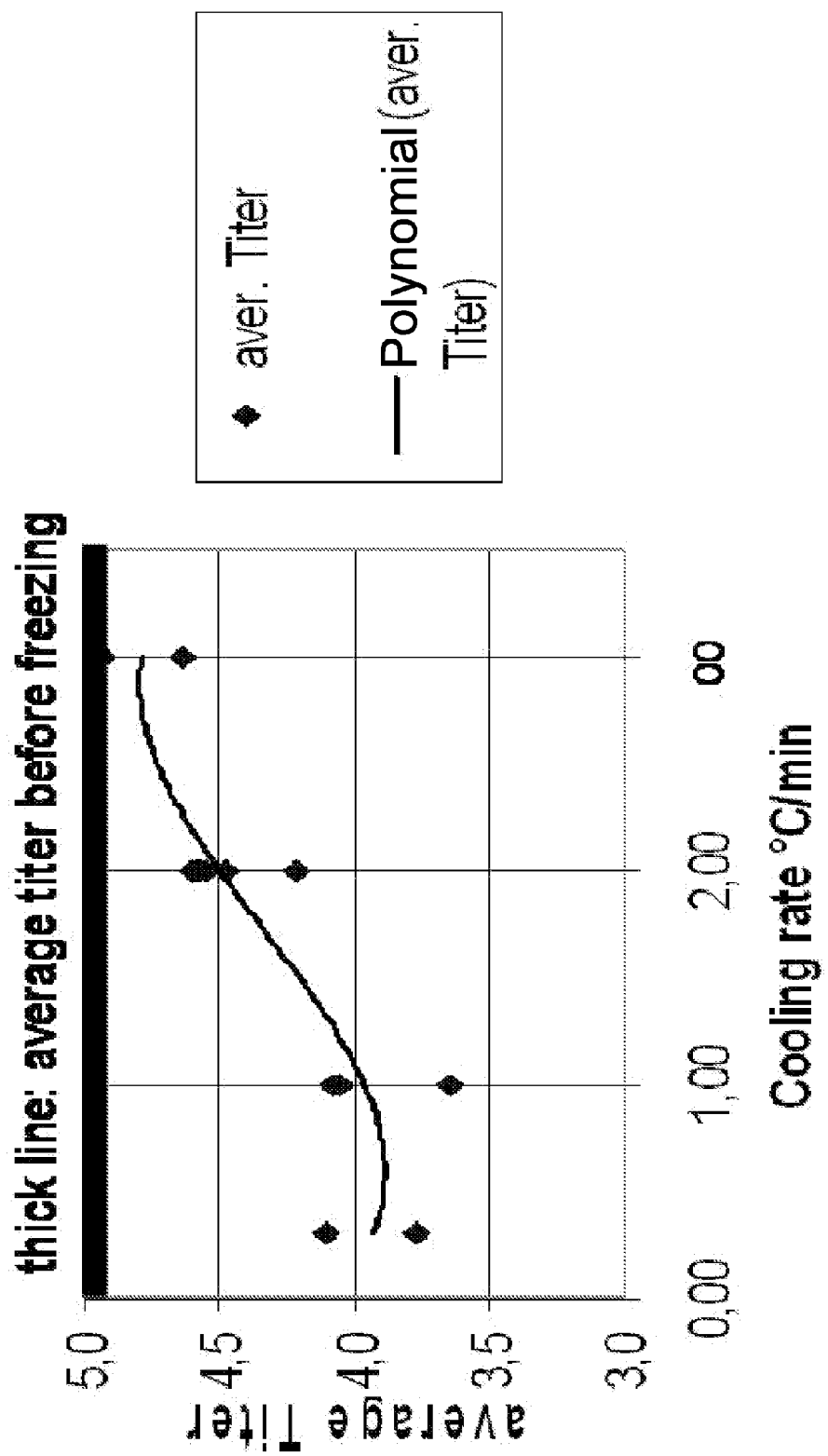
FIG. 9 shows the increase of yield in dependence on the freezing process.
Figure 10:
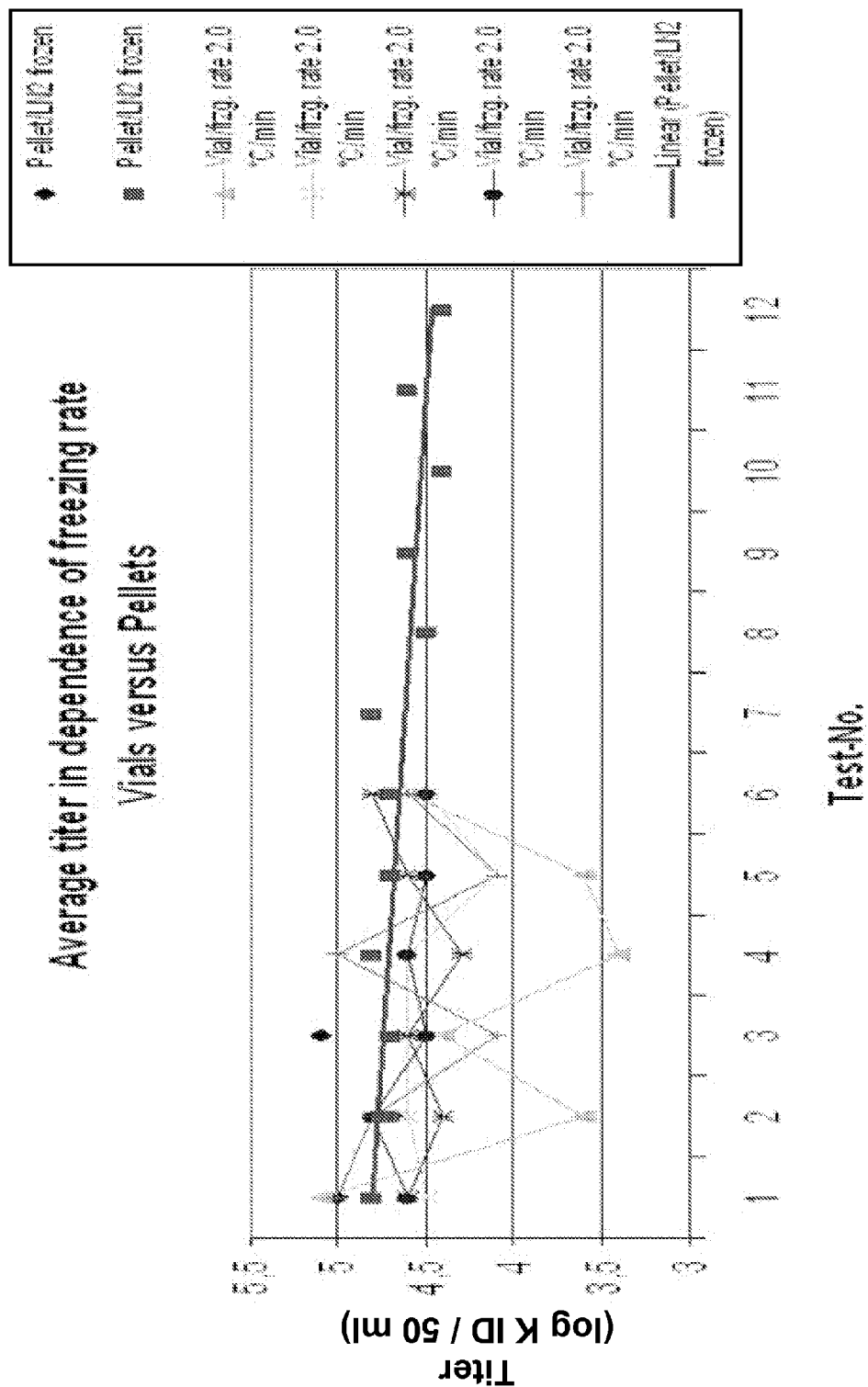
FIG. 10 shows the homogeneity of the actives in dependence upon the freezing process (vial vs pellet process).

FIGS. 7 and 8 show the difference between pellet freeze-drying and conventional freeze drying in vials. The pellets shown in FIG. 7 are in the range 500-1500 μm. The vials shown in FIG. 8 are 6 ml-vials. The pellets were prepared by dropping droplets of a liquid formulation into liquid nitrogen. The liquid nitrogen was stirred but agglomeration could not be totally avoided. Nevertheless the difference of uniformity of the agent (titer)—content (measured in log-values) between the pellets of FIG. 7 and the contents of the frozen vials of FIG. 8 is evident. The scattering of titer values of the product frozen in the vials is much higher than the very slight scattering values of the frozen pellets (FIG. 9). A comparison of average titer values in dependence on the cooling rate shows a strong influence of the cooling rate. As shown in FIG. 10, the titer values improve with increasing freezing rate.

Figure 11:
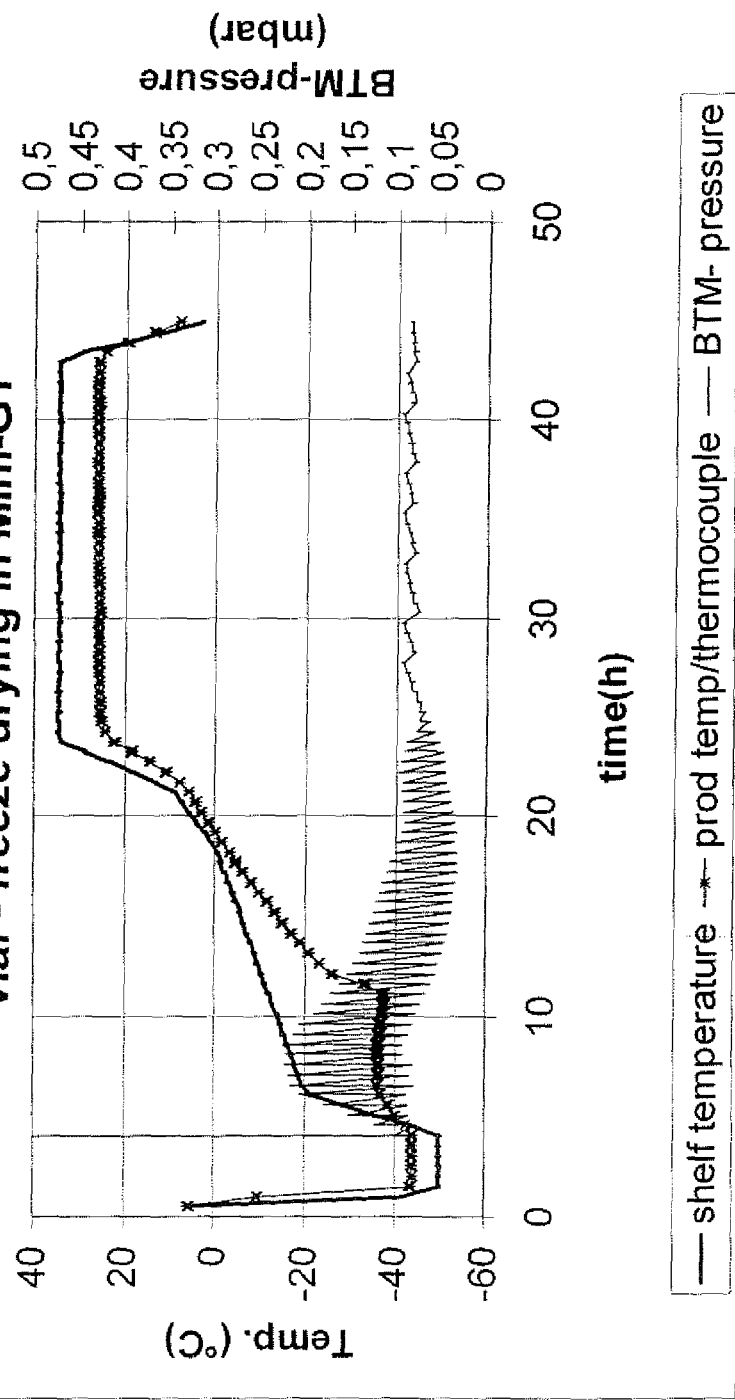
FIG. 11 shows the lyo cycle of the vial freeze drying of a vaccine.
Figure 12:
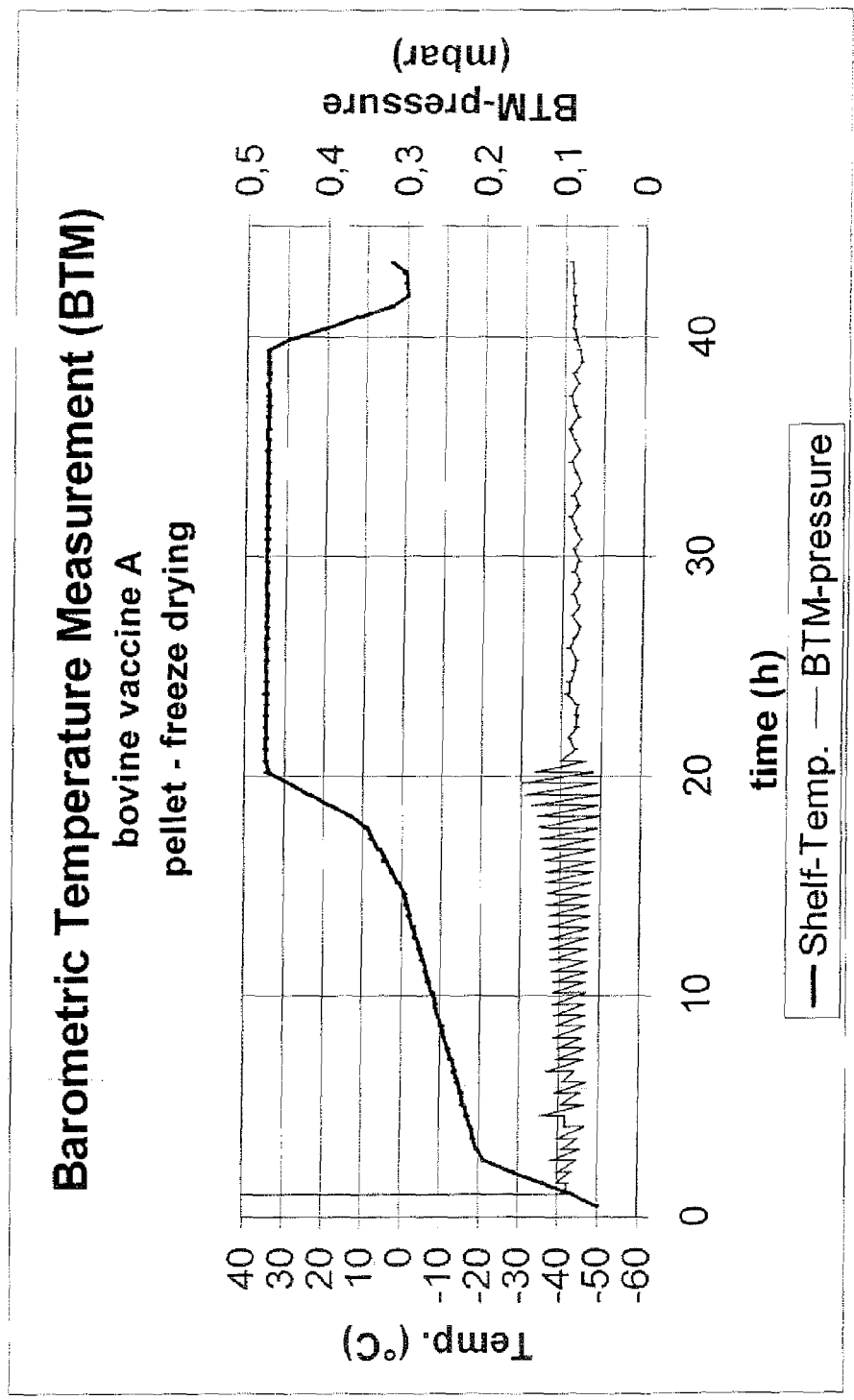
FIG. 12 shows the lyo cycle of the pellet freeze drying of a vaccine.
Figure 13:
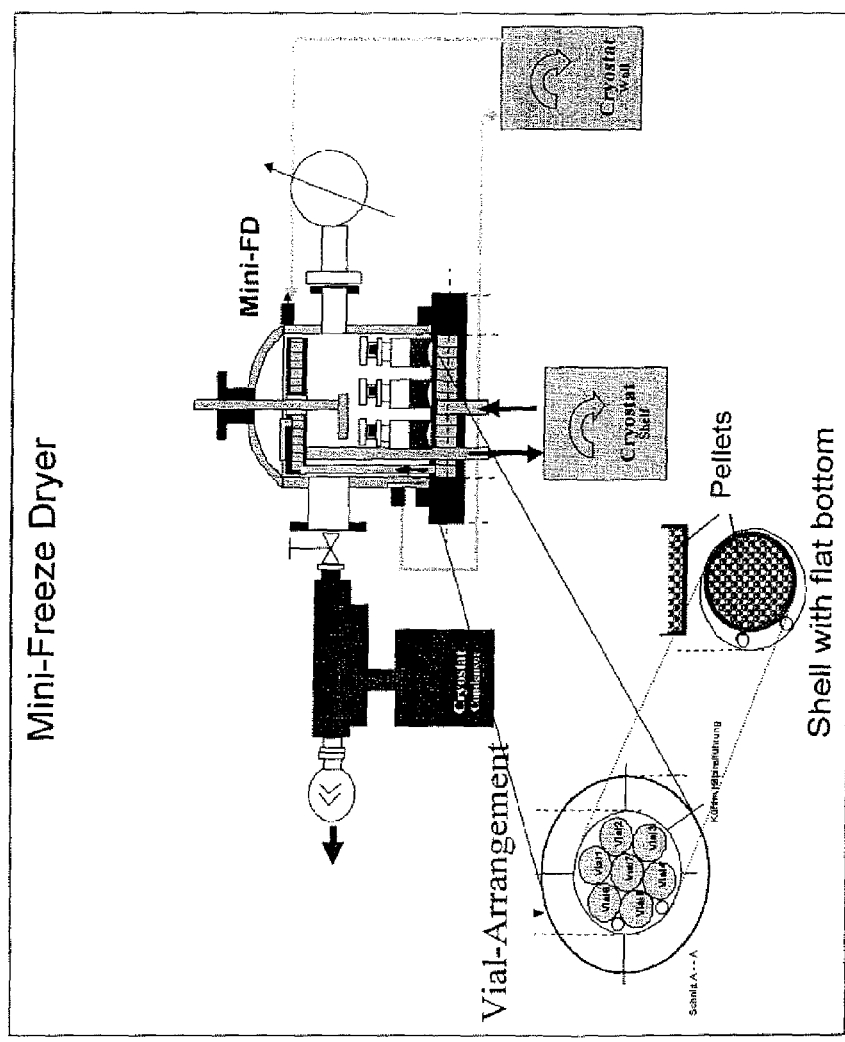
FIG. 13 is a schematic diagram of the mini-freeze dryer used to compare the present process to the conventional prior art process.
Figure 14:
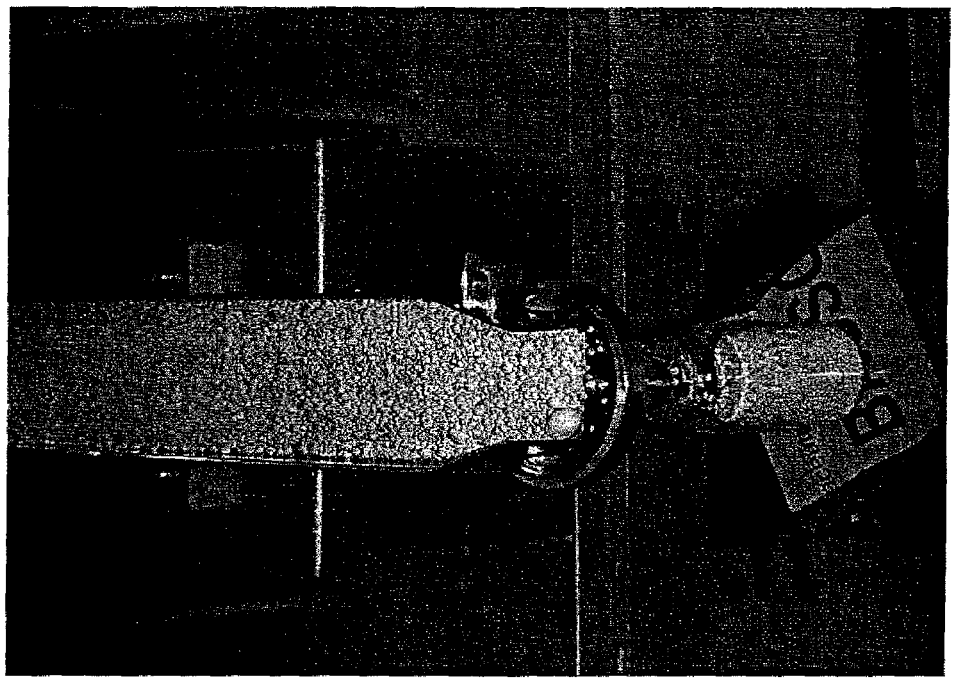
FIG. 14 is a photograph of a vibrating chute dosing machine.
Figure 15:
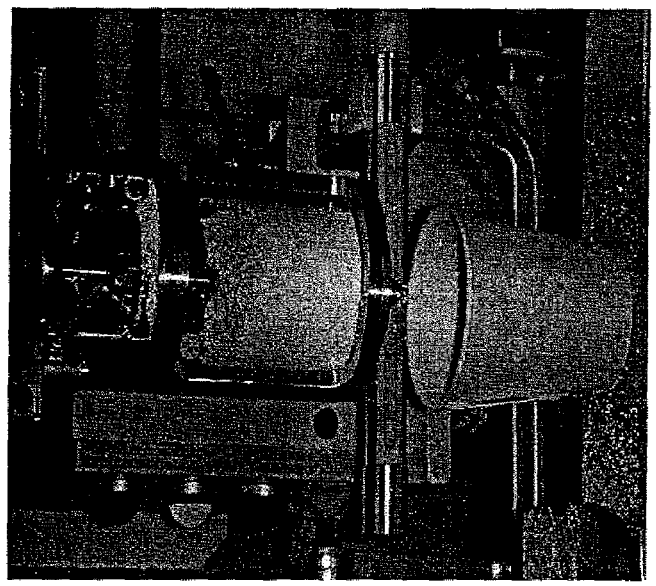
FIG. 15 is a photograph of a screw conveyer dosing machine.
Figure 16:
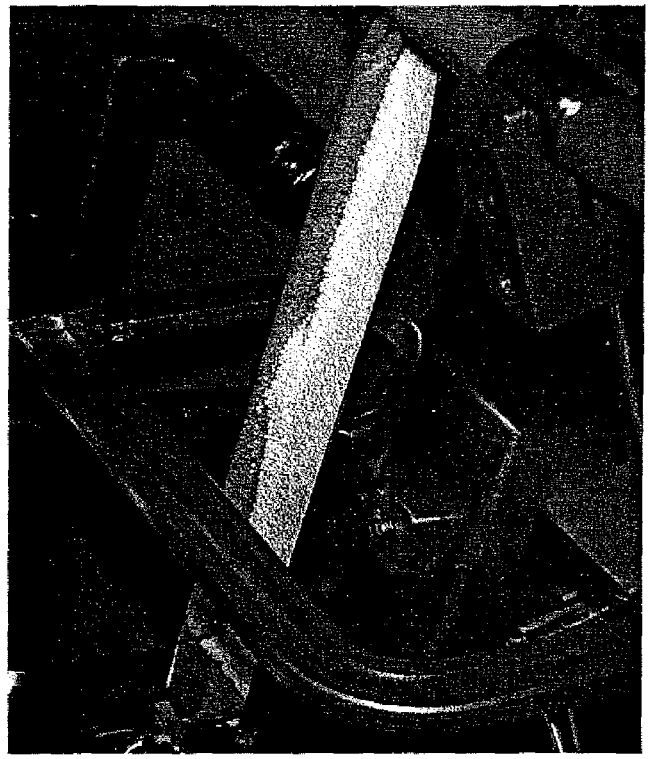
FIG. 16 is a photograph of the continuous flow of granules on a vibrating chute dosing machine hindered by electrostatic charges.
Figure 17:
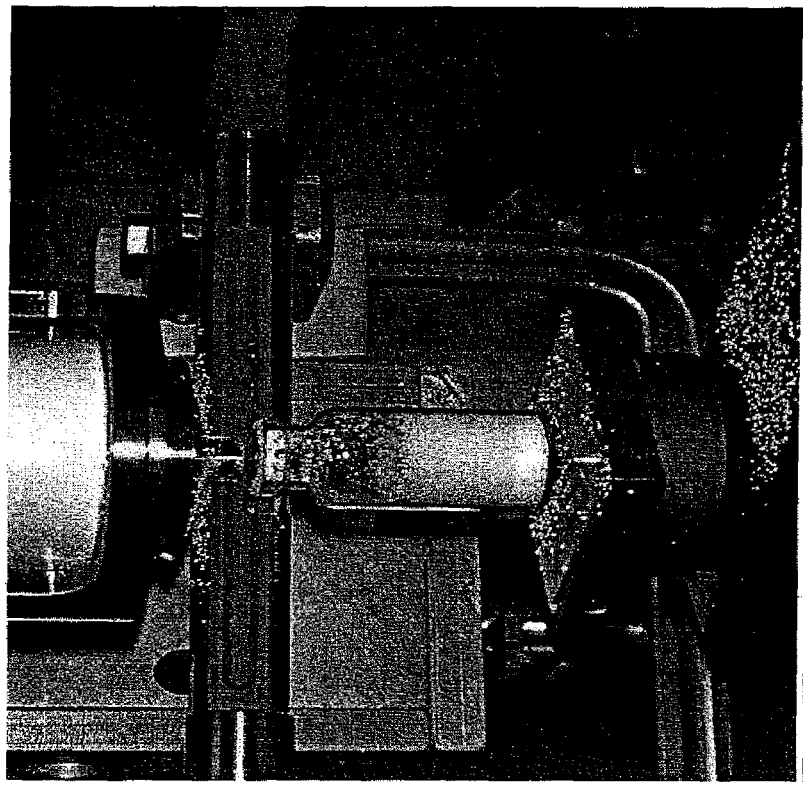
FIG. 17 is a photograph of the effects of electrostatic charges hindering the loading of granules from a screw conveyor into vials.
Figure 18:
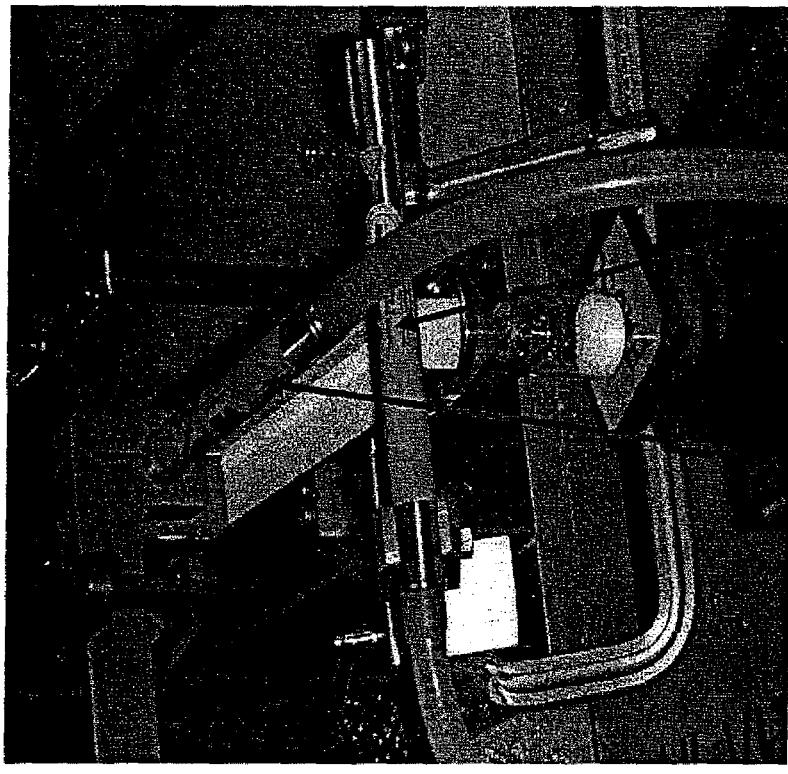
FIG. 18 is a photograph of a vibrating chute dosing machine wherein an ionizer is added to counteract electrostatic effects.

A comparison of the different freeze-drying processes (conventional freeze-drying in vials vs. pellet freezing-drying) was performed using a Mini-GT freeze-dryer (FIG. 13). This freeze dryer provides controllable freeze drying conditions. Temperature controlled walls are provided to avoid edge effects. A very fast working valve allows Barometric Temperature Measurements (BTM-measurements) for observing the drying process. For pellet freeze drying an aluminum shell with flat bottom, dressed to size for good heat conduction, was used. The height of the layer was 10 mm. FIGS. 11 and 12 show the different behavior of the two processes. The vial process shows at the beginning of the primary drying period stronger pressure rises during the BTM-measurement that means higher product temperatures at the sublimation surface while the pellet freeze drying process shows only small pressure rise when closing the drying chamber for a very short time interval (4-6 sec). This means only small temperature differences determined by the system pressure.

This example indicates that the pellet freeze-drying is a gentle process, however in this case the different freeze-drying process did not affect the titer values at all. The entire increase in yield was achieved due to the improvement of the freezing process however.

Example 2

One important difference between the pellet freeze-drying process of the present invention and the conventional vial based freeze drying process resides in the filling process. The filling of solids into containers is generally a difficult process due to the fact that the flow properties of solids are affected by a variety of properties. Additionally problems frequently arise due to electrostatic charges generated by interaction of the particles during metering in the metering device employed in the filling process. Filling of the mechanically stable pellets of the present invention is less difficult than the normally used powder fill process. The flowability of the stable pellets is orders of magnitudes better than that of powders.

To demonstrate the accuracy of the present process a series of tests were conducted using two different systems for filling solid materials, both of which are available from Bausch & Stroebel. In one of the systems a screw conveyor was used and in the other a vibrating chute was used. Both systems operated under sterile conditions.

Four tests with statistically meaningful results were conducted: each test consisted of at least 200 continuous filling procedures. Three different particle sizes were used: fine (~500 μm), coarse (~1000-2000 μm) and a mixture of both. The targeted doses were 100 mg and in one case 50 mg. The container used was a 20 ml vial.

The vibrating chute, protected against electrostatic charge by a ionizer, worked with excellent precision in every case. Maximum deviation (underfilling of targeted 100 mg/50 mg) was 2 mg. The filling frequency was about 5-6 sec vial.

Results:

As the freeze dried material has only a very small residual moisture content, electrostatic effects lead to difficulties in conveying and filling the material. The electrostatic charge caused by the screw conveyer, for example, interfered with the ability of the granules to fall into the vials. Ionization of the air did not result in significant improvements.

Electrostatic effects were also observed with the vibrating chute, especially when using the fine material. But in this case the electrostatic charge was lower than when using the screw conveyor, and ionization of the air led to a free flowing material. Furthermore, compared to the screw conveyor the vibrating chute had the advantage that the ionizer could be placed near to the surface of the granules.

In four runs (coarse material, fine material, mixed material at a dosage of 100 mg and fine material at a dosage of 50 mg) excellent results were obtained using the vibrating chute, as can be seen in FIGS. 14-18.

The vibrating chute had two conveying speeds: a fast one for dosing approximately the first 90-95% of the whole dosage and a slow one dosing the remainder with high accuracy. Time interval for a 100 mg dose was approximately 4 sec at high conveying speed and approximately 2 sec at the slower conveying speed for fine dosage. The whole dosage of 100 mg. therefore took about 6 sec. The lengths of the time intervals and the vibration frequencies are selected in accordance with the flowability of the product to be dosed.

The principle used for dosing was gravimetric. Therefore the dose error consists of two components: the error of the scale, which is ±1 mg, and the error of dosing, which is also ±1 mg. The error of dosing depends on the properties of the material, as the error results, for example, on the degree to which the granules tend to continue rolling off the chute after the vibration has been stopped. The granules used demonstrated ideal behavior in this respect. Therefore the maximum error was ±2 mg. As the control of the vibrating chute ensures at least the minimum dose, a significant overfilling can sometimes be possible if the granules are very large and fall off the chute at the end of the dosing interval. Errors in filling were observed only very seldomly in the foregoing tests. Furthermore the errors can be monitored so that over- or underfilled vials can automatically be withdrawn from the filling line. Therefore there is no need for significant overfilling with the present process in order to ensure a minimum filling. Only the error of the scale, if any, has to be compensated for by overfilling.

By mixing fine and coarse materials, a bimodal size distribution was produced to test the influence of a wide particle size distribution. The bimodality sometimes led to problems because the material built up smaller blockades at the weir through which the granules were conveyed onto the chute. The built-in controller of the vibrating chute was able to compensate these irregular blockades however. Nevertheless some underfilling events cannot be avoided in case of such blockades. The use of nearly monomodal granules with a "normal" spread of size distribution can help avoid such blockades.

TABLE 6.1 results of dosing experiments

| material | mean dose mg | dev. dose mg | No. runs — | min mg | max mg | mean time s | dev time s |
|---|---|---|---|---|---|---|---|
| coarse | 100.25 | 1.2 | 199 | 98 | 105 | 5.92 | 0.67 |
| fine | 100.00 | 0.486 | 204 | 98 | 102 | 6.53 | 0.69 |
| fine | 50.17 | 0.560 | 106 | 48 | 52 | 3.92 | 0.85 |
| mix * | 99.92 | 1.169 | 106 | 97 | 103 | 6.00 | 1.29 |
| mix ** | 100.20 | 0.850 | 69 | 98 | 103 | 5.36 | 0.72 |

* incl. correction of a blockade by controller
** without of error of blockade

We claim:

1. A process for producing a dosage of a sterile freeze-dried product in the form of pellets in a container, the amount of active ingredient of which is equal to a predetermined amount or exceeds such predetermined amount by less than 10% by weight, which comprises the steps of forming droplets by passing a solution of the product through frequency assisted nozzles and passing said droplets to an isolated tunnel supplied with a flow of cryogenic gas and allowing said droplets to fall through a counter-current flow of said cryogenic gas in said isolated tunnel to form pellets of a size which, when freeze dried, have a particle size distribution of 500 µm<$d_{50}$<1500 µm, said tunnel being long enough to provide a residence time sufficient for the cooling and freezing of the falling droplets, freeze-drying the pellets to form freeze-dried pellets having a particle size distribution of 500 µm<$d_{50}$<1500 µm, storing and homogenizing the freeze-dried pellets, assaying the freeze dried pellets while they are being stored and homogenized to determine the concentration of active ingredient in said freeze dried pellets, determining the amount of the homogenized freeze dried pellets required to provide a predetermined amount of the active ingredient and loading the freeze-dried and homogenized pellets into said container in an amount that is at least equal to and less than 10% by weight in excess of the determined amount.

2. The process of claim 1, wherein said product comprises one or more pharmaceutically or biologically active components.

* * * * *